(12) United States Patent
Boyd et al.

(10) Patent No.: US 6,469,788 B2
(45) Date of Patent: Oct. 22, 2002

(54) COHERENT GRADIENT SENSING ELLIPSOMETER

(75) Inventors: David A. Boyd, South Pasadena; Ares J. Rosakis, Altadena; David M. Owen, Redondo Beach, all of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/820,094

(22) Filed: Mar. 27, 2001

(65) Prior Publication Data

US 2002/0012122 A1 Jan. 31, 2002

Related U.S. Application Data

(60) Provisional application No. 60/192,648, filed on Mar. 27, 2000.

(51) Int. Cl.[7] .............................. G01J 4/00; G01B 11/06

(52) U.S. Cl. .......................... 356/369; 356/630; 356/73
(58) Field of Search .......................... 356/369, 364–368, 356/601, 602, 612, 630, 631, 632, 451, 453, 73; 250/225, 559.22, 559.23, 559.27

(56) References Cited

U.S. PATENT DOCUMENTS

| | | | |
|---|---|---|---|
| 3,985,447 A | | 10/1976 | Aspnes |
| 4,053,232 A | | 10/1977 | Dill et al. |
| 5,232,547 A | * | 8/1993 | Drowley et al. ............ 356/357 |
| 5,517,312 A | | 5/1996 | Finarov |
| 6,031,611 A | | 2/2000 | Rosakis et al. |

* cited by examiner

Primary Examiner—Hoa Q. Pham
(74) Attorney, Agent, or Firm—Fish & Richardson P.C.

(57) ABSTRACT

Systems and techniques for integrating an optical coherent gradient sensing (CGS) module and another optical sensing module to simultaneously measure the curvature and another property of a specularly reflective surface.

29 Claims, 3 Drawing Sheets

COHERENT GRADIENT SENSING ELLIPSOMETER

This application claims the benefit of U.S. Provisional Application No. Ser. No. 60/192,648, filed on Mar. 27, 2000.

The U.S. Government may have certain rights in this invention pursuant to Grant No. DMS-9615858 awarded by NSF/DARPA.

BACKGROUND

This application relates to optical detection of properties of a material or structure with a reflective surface.

An optical beam may be used as a probe to detect properties of various materials and structures that can interact with the optical beam. In particular, optical reflection of the optical probe beam from a reflective surface of a structure may be measured and processed to determine certain properties of that surface. For example, material parameters such as the optical absorption coefficient or the refractive index of the material that forms the surface may be measured from the optical reflection. Also, geometrical parameters of the surface, such as the thickness of a thin film that is at least partially transparent, or the curvature of the reflective surface, may be measured from the optical reflection.

Optical detection may achieve certain advantages. For example, when the power of the probe beam can be kept at a sufficiently low power level, the optical detection can be non destructive or evasive so that the properties of the measured object may be preserved. The probe beam may also be expanded to illuminate an area of a target object so that each location in the entire illuminated area may be measured at the same time. Optical detection may also be used to achieve full-field measurements at high speeds or with high accuracy.

SUMMARY

This application includes techniques and systems that integrate an optical coherent gradient sensing (CGS) module and another optical sensing module such as an optical ellipsometer to use a single probe beam to simultaneously measure properties of a specularly reflective surface. A collimated coherent optical probe beam is used to illuminate a target area on the reflective surface to obtain information on each location within the illuminated target area for measurements of both the ellipsometer and the CGS module. The reflected beam is split into a first part for the ellipsometry measurements and a second part for the CGS measurements. The ellipsometer operates to determine the optical properties of the sample. For example, refractive indices, the absorption coefficient of a thin film formed on a substrate, or the thickness of the thin film, among others, may be determined. The CGS module operates to determine the surface curvature of each location of the illuminated area. Notably, the material properties and the surface curvature of each location within the illuminated area are measured at the same location and time by extracting information from the same reflected beam from the surface under measurement. Measurements at different locations within the illuminated area are made at the same time.

DETAILED DESCRIPTION

Figure 1:
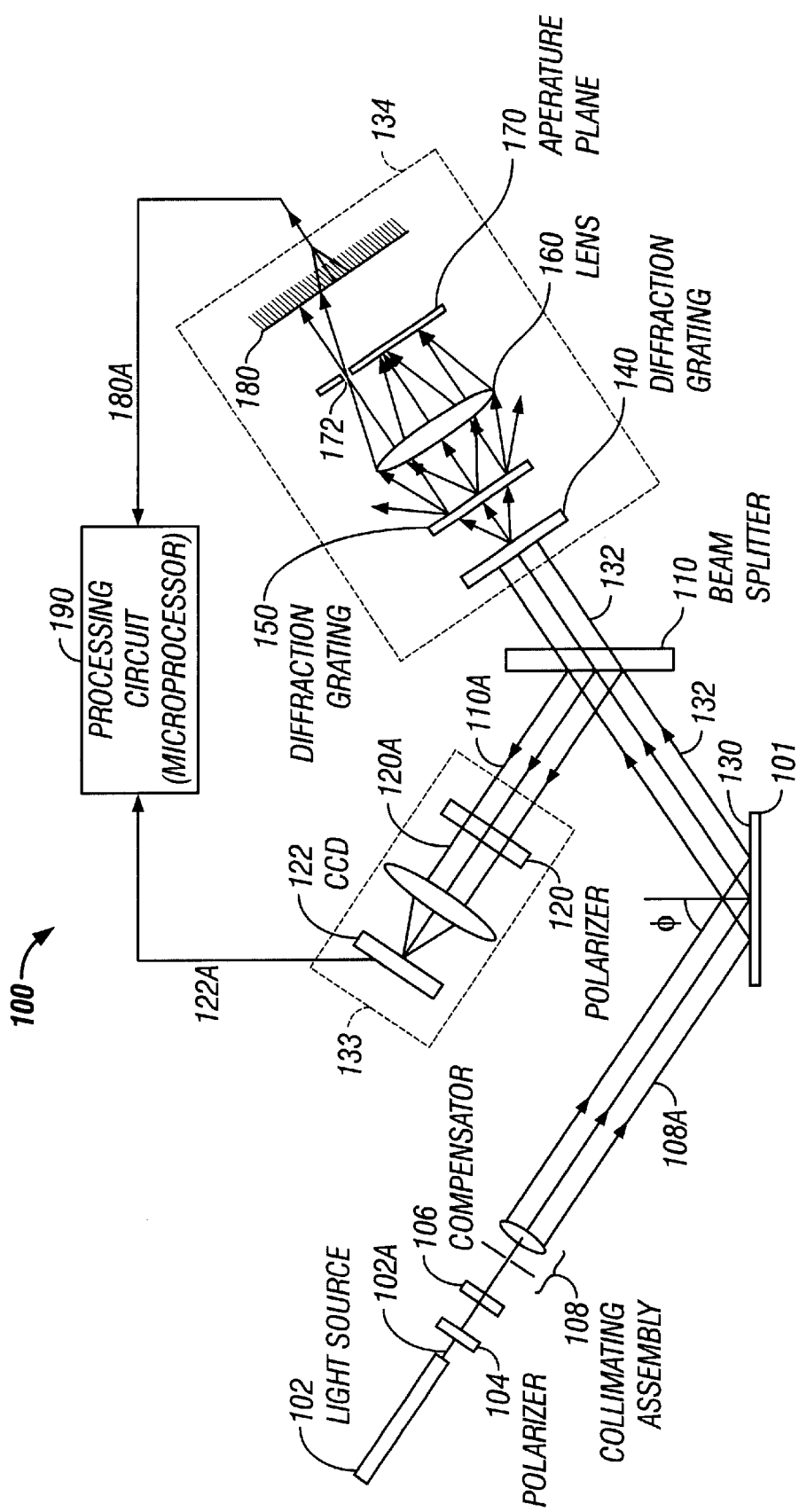
FIG. 1 illustrates the optical layout of an optical coherent gradient sensing (CGS) ellipsometer according to one embodiment.

Ellipsometry measures a change in the state of polarization of a reflected or transmitted beam from the state of polarization of an incident beam caused by reflection or transmission of a sample material. When the reflected beam is measured, the surface of the sample material is generally a specularly reflective surface. This change in the state of polarization may be represented by two parameters, the amplitude and the phase of the complex reflectance ratio of the illuminated spot. When the reflective surface is a bare substrate, ellipsometry may be used to determine the refractive index and absorption coefficient of the substrate. If the reflective surface includes a thin dielectric film formed over a substrate, then two unknown parameters of the film and the substrate may be determined. For example, the two parameters may be any two of the refractive indices and absorption coefficients of the film and the substrate and the thickness of the substrate.

The ellipsometry technique may be used with an expanded and collimated optical beam for illuminating a target area so that an ellipsometric image may be obtained from the reflected beam to represent the change in polarization caused by different spots in the illuminated target area. See, e.g., Jin et al., Imaging Ellipsometry Revisited: Developments for Visualization of Thin Transparent Layers on Silicon Substrate, Review of Scientific Instruments, Vol. 67(8), 2930–2936 (August, 1996). This full-field imaging technique may be used to eliminate the need for scanning the probe beam over a target area to measure one location at a time and to increase the processing speed.

Ellipsometry by itself, however, cannot measure the surface curvature of the illuminated spot. The surface curvature is an important parameter in part because it can be used to analyze surface stress caused by a change in temperature or integration of parts with different mechanical, physical and thermal properties. Stresses may lead to degradation or even failure in device performance and adversely affect the long-term reliability of some integrated devices such as integrated circuits, electro-optical devices, and MEMS devices which typically include multiple layers of dielectrics and metals on a semiconductor substrate.

In addition, the curved surfaces can also pose problems for determining the ellipsometric parameters. For example, for certain materials such as Si, the ellipsometric parameters are strong functions of the angle of incidence, especially near the Brewster angle. For full field ellipsometry in applications, it is generally difficult to accurately determine the ellipsometric parameters without knowing the curvature of the surface. For example, if an initially highly collimated incident beam and the sample surface is flat, the incident angle is known. When the sample surface is locally curved, different rays of the collimated input beam may have different incident angles that vary from location to location throughout the incident beam. The curvature of the sample surface is needed in order to determine the incident angles at different locations on the surface and hence to obtain proper ellipsometric parameters.

The curvature measurement may be implemented simultaneously by using an optical coherent gradient sensing (CGS) technique where the wavefront of a reflected beam is processed to obtain the curvature information of the illuminated spot. U.S. Pat. No. 6,031,611 to Rosakis et al. When the reflective surface is curved, the wavefront of the reflected probe beam is distorted and thereby the reflected probe beam acquires an optical path difference or phase change associated with the curvature of the surface under measurement. A first grating diffracts the reflected probe beam to spatially separate diffraction components of different spatial frequencies. A second grating further diffracts each diffraction component produced by the first grating. An optical element (e.g., a lens) is positioned relative to the second grating and combines two selected diffraction components produced by the second grating by diffracting two different diffraction components produced by the first grating. The two selected diffraction components are substantially parallel to each other and are directed to overlap and interfere with each other to produce an interference pattern. The diffraction by the two gratings effectuates a relative spatial displacement between the two selected diffraction components. This allows for extraction of a spatial gradient of the phase distortion caused by the curvature of the reflective surface from the interference pattern. This spatial gradient, in turn, can be further processed to obtain the curvature information.

FIG. 1 shows one embodiment 100 of an optical coherent gradient sensing (CGS) ellipsometer based on a combination of the ellisometry and the CGS technique. A sample stage 101 is used to hold a specimen surface 130 which is specularly reflective and not optically diffusive. The reflective specimen surface 130 can be a uniformly smooth or polished surface or have reflective segments to form patterns and structures therein.

A light source 102 such as a laser produces a coherent optical probe beam 102A. A polarizer 104 and an optical phase compensator 106 are placed in the optical path of the beam 102A to control the polarization of the input beam 102A. An optical collimator 108 is positioned between the compensator 106 and the sample stage 101 to collimate and expand the beam 102A to produce an expanded, collimated probe beam 108A. The incident angle of the beam 108A is controlled at a desired angle to facilitate the measurements. The specimen surface 130 reflects the probe beam 108A to produce a reflected probe beam 132.

A beam splitter 110 is placed in the optical path of the reflected probe beam 132 to split a portion of the reflected beam 132 as a first beam 110A to an ellisometry detector 133 for ellipsometry measurements. The remaining portion of the reflected probe beam 132, still represented by the numeral 132 in FIG. 1, is directed into a CGS detector 134 for the CGS measurements. This system allows for the simultaneous monitoring of the curvature of the surface 130 and a change in the polarization state of the reflected beam caused by the surface 130.

The ellipsometry detector 133 may include a polarization analyzer 120 and a photosensitive detector array 122 such as a CCD array. For a given set of angles for the polarizer 104 and the analyzer 120, the spatial power variation in the transmitted beam 120A through the analyzer 120 represents a spatial variation in a non-curvature property of the specimen surface 130, such as a thickness of a thin film, a refractive index, an optical absorption coefficient of the film, or a combination thereof. The detector array 122 includes an array of sensing pixels. Each sensing pixel uniquely corresponds to a spatial location in the illuminated area of the surface 130 and receives reflected light from that location. Therefore, the pixel signals of the detector array 122 represent an ellipsometry image of the illuminated area in the surface 130. A lens imaging system 121 may be positioned in the optical path between the array 122 and the polarizer 120 to reduce the image size.

The CGS detector 134, although receiving essentially the same beam as the ellipsometry detector 133, is configured to extract completely different information content in the reflected probe beam 132. A pair of gratings, 140 ($G_1$) and 150 ($G_2$) are separated from each other by a specified distance, $\Delta$, and are placed in the optical path of the beam 132. The reflected probe beam 132 is diffracted by the gratings 140 and 150 to produce multiple diffracted orders. An optical element 160 is positioned relative to the grating 150 to combine at least two selected diffraction orders produced by the grating 150 by diffracting two different diffraction orders produced by the grating 140. The two selected diffraction components interfere with each other to produce an interference pattern. A lens may be used as the optical element 160 to select certain diffraction orders produced by the grating 150 to form distinct diffraction spots on a filter plane 170 which is spaced from the lens by about its focal length.

A spatial filter 172, such as an aperture as shown, is placed in the filter plane 170 to select a diffraction order of interest and block other signals. The selected diffraction order is then imaged through an imaging lens onto a photosensing device which may include a semiconductor photosensing array of multiple photosensing pixels (e.g., a CCD array) or a photosensing medium (e.g., a photographic film). A camera 180 is shown to represent a combination of the imaging lens and the photosensing medium. The imaging lens may be used to reduce the image size. The output signal from the camera 180 is processed by a signal processor 190 to extract the curvature information. The signal processor may include a microprocessor which is programmed to perform the data processing. The operation of the light source 110 may also be controlled by the signal processor.

The wavefront of the reflected probe beam 132 is modified by the specimen surface 130 and has information on the surface curvature. The diffraction by the two gratings 140 and 150 effects a relative spatial displacement between the two selected diffraction orders produced by the grating 150. This allows for extraction of a spatial gradient of the phase distortion caused by the curvature of the reflective surface from the interference pattern. This spatial gradient, in turn, can be further processed to obtain the curvature information.

The two gratings 140 and 150 in general may be any gratings, with different grating periods and oriented with respect to each other at any angle. Preferably, the two gratings may be oriented with respect to each other in the same direction and may have the same grating periods to simplify the data processing.

Figure 2:
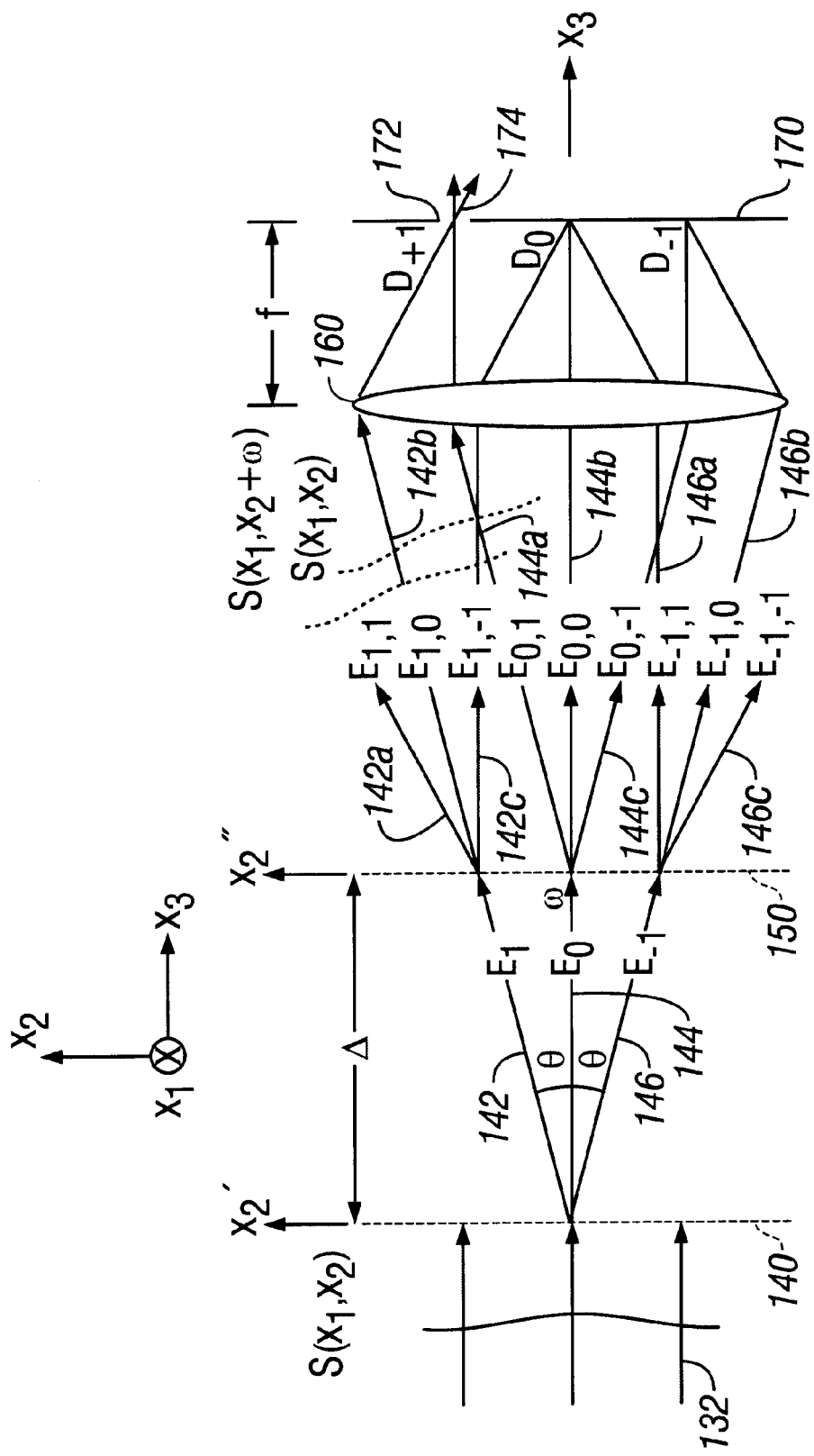
FIG. 2 illustrates the operation of the coherent gradient sensing module for extracting curvature information from the reflected beam by using two identical gratings aligned parallel to each other.

FIG. 2 illustrates the operating mechanism of the CGS detector 134 shown in FIG. 1 in two dimensions by using two identical gratings 140 and 150 aligned parallel to each other. Consider a Cartesian coordinate system ($x_1$, $x_2$, $x_3$) in which the $x_2$ axis is parallel to the grating rulings of both the gratings 140 and 150.

The grating 140 ($G_1$) diffracts the reflected probe beam 132 into several diffraction waves denoted as $E_0$, $E_1$, $E_{-1}$, $E_2$, $E_{-2}$, etc. For illustrative purpose, only the first three diffraction orders, i.e., zero-order wave 144 ($E_0$), +1-order 142 ($E_1$), and −1-order wave 146 ($E_{31\ 1}$) are shown. Each of these wave fronts is further diffracted by the second grating 150 ($G_2$) to generate multiple wavefronts. For example, the +1-order 142 ($E_1$) is diffracted to produce wavefronts 142a ($E_{1,1}$), 142b ($E_{1,0}$), 142c ($E_{1,-1}$), etc.; zero-order 144 ($E_0$) is diffracted to produce wavefronts 144a ($E_{0,1}$), 144b ($E_{0,0}$), 144c ($E_{0,-1}$), etc.; and −1-order 146 ($E_{-1}$) is diffracted to produce wavefronts 146a ($E_{-1,1}$), 146b ($E_{-1,0}$), 146c ($E_{-1,-1}$), etc.

Certain diffracted beams generated by the grating 150 from different diffraction orders generated by the grating 140 are parallel since the two gratings 140 and 150 are identical. This could also occur when the ratio of the grating periods of the two gratings 140, 150 is an integer. Under such conditions, a lens can be conveniently used as the optical element 160 to overlap various sets of parallel diffracted beams emerged from the grating 150 with one another at or near the filtering plane 170 to form multiple diffraction spots. These diffraction spots have interference fringes due to the interference of the overlapped beams. The interference fringes have information indicative of the gradient of the phase distortion in the wavefront of the reflected probe beam 132.

For example, the zero-order diffraction beam 142b ($E_{1,0}$) originated from the beam 142 is parallel to the +1-order diffraction beam 144a ($E_{0,1}$) originated from the beam 144. These two beams 142b and 144a are focused to a point 174 ($D_{+1}$) on the filter place 170 by the lens 160. Similarly, the diffracted beams 142c and 144b overlap and interfere with each other to form a spot $D_0$, and beams 144c and 146b overlap and interfere with each other to form a spot $D_{-1}$, respectively.

The interference pattern of any of these spots has the information of the gradient of the phase distortion in the wavefront of the reflected probe beam 132 and can be used to determine the curvature of the specimen surface 130. The example in FIG. 2 shows the spot 174 ($D_{+1}$) is selected by the aperture 172 in the filter plane.

Assume that the wavefront of the reflected probe beam 132 is approximately planar and has a local phase variation $S(x_1, x_2)$. The net effect of the diffraction by the gratings 140 and 150 is to produce a lateral shift, or "shearing", of the incident wave front along the direction of the gratings, i.e., in the $x_2$-direction. For example, the wavefront of the diffracted beam 142b ($E_{1,0}$) is shifted by an amount, ω, along the $x_2$-direction as compared to the wave front of the diffracted beam 144a ($E_{0,1}$) so that the wavefronts of the beams 142b and 144a are given by $S(x_1, X_2+\omega)$ and $S(x_1, x_2)$, respectively. The wave front shift is parallel to the principal axis of the gratings, i.e. along $x_2$ if the grating lines are oriented along $x_1$ as shown in FIG. 2.

The magnitude of the spatial shift ω is a function of the grating separation, Δ, and the diffraction angle, θ, which is identical in both gratings 140 and 150:

$$\omega = \Delta \tan \theta.$$

where the diffraction angle, θ, is determined by the wavelength λ of the reflected probe beam 132 and the grating period, p, according to the following relation:

$$\theta = \arcsin \frac{\lambda}{p}.$$

For shallow surfaces with gradual curvature variation, i.e., the secondary derivative of the surface profile over surface position is much less than 1, the curvature tensor can be approximately written as, $$\kappa_{\alpha\beta}(x_1, x_2) \approx \frac{\partial^2 f(x_1, x_2)}{\partial x_\alpha \partial x_\beta}$$

$$\approx \frac{p}{2\Delta}\left(\frac{\partial n^{(\alpha)}(x_1, x_2)}{\partial x_\beta}\right), n^{(\alpha)} = 0, \pm 1, \pm 2, ...$$

where, α, β are 1 or 2. Hence the curvature tensor is directly related to the gradients of a CGS interferogram. For a given CGS system with certain parameters p and Δ, the curvature at any location on a specimen surface can be determined by measuring the number of fringes per unit length in desired directions. Thus, a CGS interferogram provides a full field technique for determining the instantaneous value of the specimen curvature tensor at any point, ($x_1$, $x_2$).

Referring back to FIG. 1, the CGS ellipsometer 100 further uses a processing circuit 190 to receive and process signals 122A and 180A from the detector arrays 122 and 180, respectively. A microprocessor may be included in the circuit 190 for data processing.

In processing the CGS signal 180A, the circuit 190 may be programmed to perform the following signal processing operations. First, the CGS image of a specimen is digitized. Then, a coordinate system is assigned to the CGS image such that each location on the surface of the specimen is registered in the coordinate system and the coordinates of the CGS image have a known relation with the actual specimen dimensions. Next, the distribution of the CGS infringes as a function of the coordinates in the assigned coordinate system is determined. For a shallow surface, a local Cartesian coordinate system ($x_1$, $x_2$) can be used and fringe distribution functions $n^{(1)}(x_1, x_2)$ and $n^{(2)}(x_1, x_2)$ respectively corresponding to two mutually orthogonal directions $e_1$ and $e_2$ can be determined. Subsequently, partial derivatives of the fringe distribution functions $n^{(1)}(x_1, x_2)$ and $n^{(2)}(x_1, x_2)$ with respect to $x_1$ and $x_2$ are computed to obtain $\partial n^{(1)}/\partial x_1$, $\partial n^{(1)}/\partial x_2$, $\partial n^{(2)}/\partial x_1$, and $\partial n^{(2)}/\partial x_2$. Finally, the curvature tensor elements $\kappa_{11}$, $\kappa_{12}$, $\kappa_{22}$ and $\kappa_{21}$ are calculated for each and every location in the specimen surface to produce the curvature map of the specimen surface ed for further analysis (e.g., stress analysis).

The CGS detector 134 shown in FIG. 1 has two gratings 140 and 150 to perform the spatial shearing of different diffraction orders. The rulings of the two gratings are parallel so that the spatial shearing is perpendicular to the rulings. The spatial shearing may be performed in at least two different directions such as two orthogonal directions to obtain the curvature map of a surface. One way to achieve spatial shearing in two directions is to place the specimen 130 on a rotating stage in the system 100. A CGS interferogram for one shearing direction is first obtained. The specimen 130 is then rotated to another direction, e.g., an orthogonal direction, to obtain a second CGS interferogram for the second direction.

Figure 3:
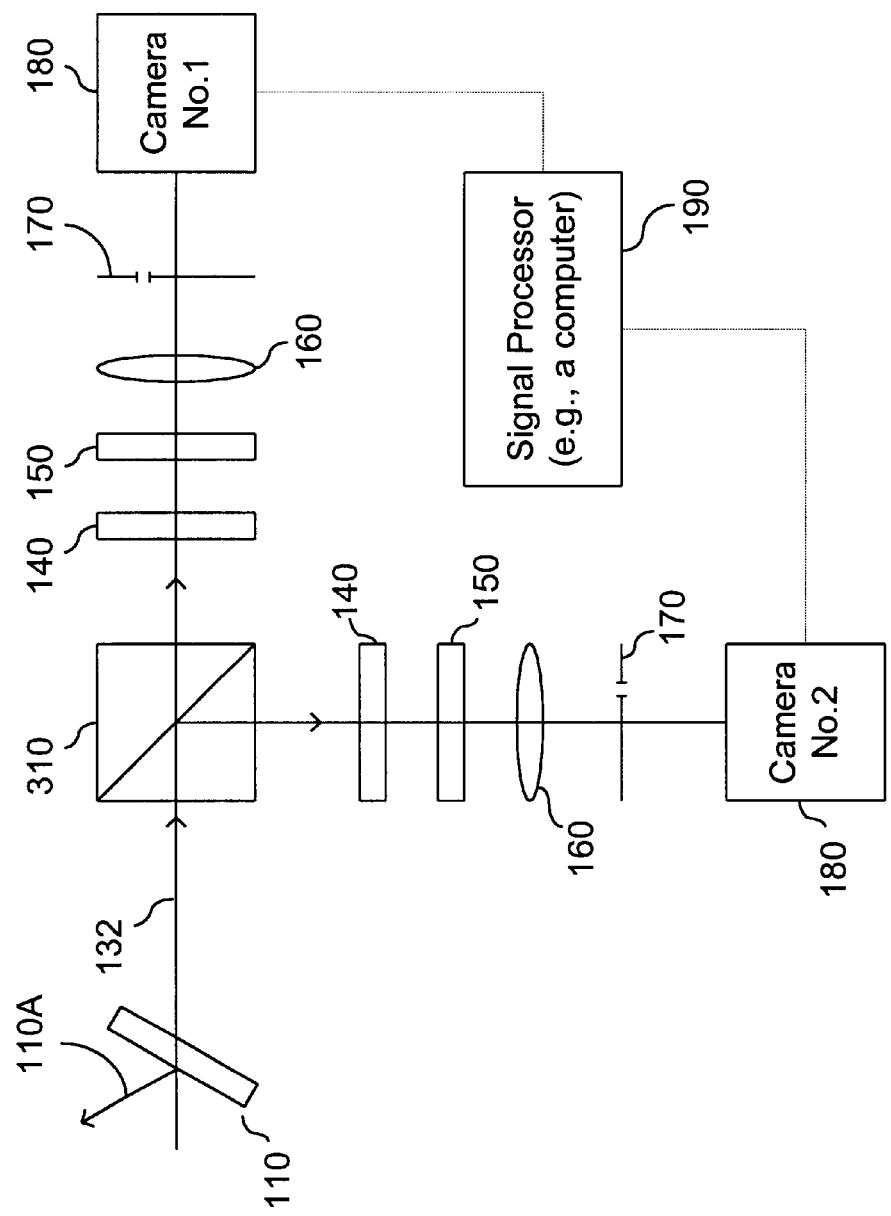
FIG. 3 shows another embodiment of the CGS detector having two optical arms for two different shearing directions.

Another way uses two separate optical arms to simultaneously perform the spatial shearing in two directions. FIG. 3 is a diagram showing one embodiment having two optical arms. A beam splitter 310 splits the reflected probe beam from the specimen 130 into two beams that are sent into two different optical arms. The two gratings in each optical arm may be parallel to each other but are perpendicular to the grating direction of another arm. This configuration can be configured to obtain CGS interferograms in two different shearing directions in essentially the same time so that time-varying effects on the curvature of the specimen surface 130 can be properly measured.

Upon completion of the curvature measurement, the processing circuit 190 can then process the ellipsometric data based on the curvature map of the surface 130 to correct errors associated with the surface curvature and thus compute the ellipsometric parameters for each and every location within the illuminated area on the surface 130. This is because the ellipsometric parameters are sensitive to the angle of incidence so that the curvature must be known to accurately determine the optical properties. First, based on the known curvature for each location on the surface 130, the directions of reflected beams from different locations on the surface can be determined. Secondly, since the location and orientation of the beam splitter 110, the polarizer, the optional lens 121, and the array 122 are known, the locations of the reflected beams received on the array 122 can be uniquely associated to the locations on the surface 130. Based on the above information, the circuit 190 can compute the ellipsometric parameters associated with different locations on the surface 130 based on the relative orientations, azimuth angles, of the elements 104, 106, and 120 for producing a minimum intensity in the beam 120A at these locations.

In operation, the CGS ellipsometer 100 is calibrated. Initially, the beam is referenced to an optically flat mirror as the surface 130. The polarization components are adjusted so that the image from the reference mirror is completely nulled at the detector array 122. The CGS components in the detector 134 are adjusted to produce completely constructive interference or an image with no fringes. Subsequent film deposition, will for many common deposition material, change the polarization state of the reflected light, these changes will be evidenced by changes in the image intensity.

Notably, the CGS ellipsometer 100 uses the same incident illumination beam 108A to obtain information on both the curvature and the ellipsometric parameters at the same time. Hence, this single operation replaces what would otherwise two separate measurements, one on the surface curvature and another on the ellipsometric parameters. If two separate operations were used, errors could coocur from the mismatch between the exact locations of measurement and also possibly from temporal variations. This system can significantly reduce or eliminate the errors in spatially correlating the curvature map to the ellipsometric map since there is no change in the position of the sample surface 130 relative to the incident beam 108A. When the sample surface 130 constantly changes, this system can also significantly reduce or eliminate the errors in temporarily correlating the curvature map to the ellpsometric map since, the information for the curvature and the information for the ellispometric measurements are obtained and updated from the reflected beam 132 at the same time. As the surface 130 changes, the measurements obtained in both the CGS detector 134 and the ellipsometric detector 133 also change and are updated. Hence, the present technique may be used for in-situ measurements in real time, such as in semiconductor fabrication, where the CGS measurements may be used to determine the surface curvature, the change in surface curvature, and the ellipsometric measurements may be used to measure the spatial distribution of the relative film thickness and film parameters such as refractive index and the optical absorption.

The CGS ellipsometer may be used to determine associated stress distribution on the surface due to deposition of films since both film thickness and curvature may be needed to determine the film stress. Other properties, such a change in stress caused by the changing film thickness, changes in material properties and their association with the stress, may also be monitored.

Further, when the CGS ellipsometer 100 is calibrated, it may be used examine the degree of collimation of the incident beam 108A by using a uniform and flat reflective reference surface 130. A beam which is not well collimated will not have a uniform angle of incidence and will give errors in the ellipsometric parameter values or false curvature measurements of the surface 130. Such errors can be used to determine the degree of the beam collimation.

The CGS ellipsometer 100 in FIG. 1 uses a null-ellipsometric arrangement. In a null ellipsometer arrangement, the relative azimuth angles of the polarizer 104, compensator 106, and the analyzer 120 are adjust such that the light reaching the detector is at a minimum or zero in an ideal case. Also, the relative retardation of the compensator 106 may be adjusted as well to locate the position at which the intensity of light received by the detector array 122 is minimum. The compensator 106 may also be located in the optical path of the beam 110A between the analyzer 120 and the beam splitter 110 or be replaced by a rotator modulated optical rotator.

The ellipsometric configuration in the system 100 may also be configured in a photometric ellipsometric mode based on measuring variation in the detected light with changing one of ellipsometric parameters. The parameter may be statically or dynamically changing. A typical example is the rotating analyzer ellipsometer. In one embodiment, the analyzer 120 in the above null ellipsometer is engaged to a rotating device to rotate at a given angular frequency. In another embodiment, the compensator 106 may be replaced by a retardation element whose retardation can be varied with time, such as a photoelastic modulator.

It is further contemplated that, the ellipsometric detector module 133, under certain circumstances, may be used to measure the sign of the surface curvature at each location within the illuminated area on the surface 130. For example, if the thickness of a thin film formed on the surface 130 is known, the additional optical path traveled at different parts of a curved film can be used to infer the sign of the curvature, e.g., concave or convex. For another example in an in-situ operation where the film is evolving or being deposited on a substrate, the variation of measured optical path with time can also be used to infer the sign of curvature.

The above system 100 in FIG. 1 may be simplified so that the detector 122 measures the reflected beam 120A without the full ellipsometric measurements. For example, the polarization elements 104, 106, and 120 may be removed. The incident beam 108A may be unpolarized. The detector array 122 is used to measure changes in absolute reflectance, typically done during film growth to monitor rate of deposition. In full field measurements, this system could provide useful relative deposition information or coverage can be performed at multiple angles.

In another simplified version of the system 100, the input beam 108A is polarized, typically P polarized along a direction parallel to the incidence plane at the surface 130. The reflected light is directly received by the detector array 122 without the analyzer 120 so that changes in the absolute intensity of the reflected polarized light are recorded. This scheme may be particularly useful when incident at the Brewster or pseudo Brewster angle for a given material. A polarized light source such as a laser may be used the light source 102. The polarizer 104 may be used to control the input polarization.

Although the present disclosure only includes a few embodiments, it is understood that various modifications and enhancements may be made without departing from the following claims.

What is claimed is:

1. A system, comprising:
a sample stage configured to hold a sample which has a specularly reflective surface;
an input module configured and positioned to produce and direct a substantially collimated coherent input probe beam incident to the reflective surface at an incident angle, optical reflection at the reflective surface producing a reflected probe beam;
a beam splitter positioned in an optical path of said reflected probe beam to transmit a portion of said reflected probe beam as a first reflected probe beam and to reflect another portion of said probe beam as a second reflected probe beam;
a first detector module positioned to receive said first reflected probe beam and operable to measure curvature of the reflective surface; and
a second detector module positioned to receive said second reflected probe beam and operable to measure properties of the sample.

2. The system as in claim 1, wherein said first detector module includes two optical gratings disposed process said first reflected probe beam and a first optical detector to receive an output from said two optical gratings.

3. The system as in claim 2, wherein said input module is configured so that said input probe beam is polarized, and wherein said second detector module includes a polarization analyzer to receive said second reflected probe beam and an optical sensing array with a plurality of optical sensing pixels to receive transmission of said polarization analyzer.

4. The system as in claim 3, further comprising a processing circuit coupled to receive output signals from said first and said second detector modules and operable to process information from said second detector module based on said measured curvature from said first detector module to extract information of the sample at each location that is associated with curvature at said each location.

5. The system as in claim 3, further comprising a rotating device engaged to said polarization analyzer to rotate said analyzer.

6. The system as in claim 3, wherein said input module includes an optical retardation element operable to produce a time-varying phase retardation on said input probe beam.

7. The system as in claim 1, wherein said input module and said second detector module are configured to form an ellipsometer to measure a change in a state of polarization of said input probe beam.

8. The system as in claim 7, wherein said ellipsometer is a null ellipsometer.

9. The system as in claim 7, wherein said ellipsometer is photometric ellipsometer.

10. The system as in claim 7, wherein said first detector module includes:
first and second gratings spaced relative to each other in an optical path of said first reflected probe beam and configured to produce a predetermined phase manipulation on a wavefront of said first reflected probe beam;
a lens positioned to receive said first reflected probe beam from said first and second gratings and configured to select and combine two diffraction components from said second grating to produce an interference pattern, wherein said selected two diffraction components are produced by said second grating from diffracting two different diffraction components from said first grating and are substantially parallel to each other; and
an optical sensing device disposed relative to said lens to receive said interference pattern and produce an electrical signal indicative of said interference pattern.

11. The system as in claim 10, further comprising a signal processor connected to receive said electrical signal and configured to extract a spatial gradient information on the wavefront of said reflected probe beam caused by a curvature of the reflective surface, wherein said signal processor determines said curvature of the reflective surface according to said spatial gradient information and processes information from said second detector module based on said curvature to determine a property of the sample.

12. A system, comprising:
a light source configured to produce and direct a substantially collimated coherent input probe beam;
a sample stage configured to hold a sample which has a specularly reflective surface and positioned in an optical path of said input probe beam, the reflective surface reflecting said input probe beam to produce a reflected probe beam;
a polarizer positioned to receive said input probe beam and control a polarization of said input probe beam incident to the reflective surface at an incident angle;
a beam splitter positioned in an optical path of said reflected probe beam to transmit a portion of said reflected probe beam as a first reflected probe beam and to reflect another portion of said probe beam as a second reflected probe beam;
a first detector module positioned to receive said first reflected probe beam and comprising two spaced optical gratings through each of which said first reflected probe beam is diffracted, and a first optical sensing array to receive a selected optical signal from diffracted signals from said two optical gratings, said first detector module operable to measure curvature of the reflective surface;
a second detector module positioned to receive said second reflected probe beam and comprising a polarization analyzer and an optical sensing array, said second detector operable to measure a change in polarization in said reflected probe beam caused by the sample; an optical phase compensator disposed in an optical path between said polarizer and said polarization analyzer in said second detector module to control polarization of said second reflected probe beam incident to said polarization analyzer; and
a processing circuit coupled to said first and said second detector modules to determine a property of the sample based on said curvature and said change in polarization.

13. The system as in claim 12, wherein said optical phase compensator is configured to produce a time-varying retardation on said second reflected probe beam.

14. The system as in claim 12, wherein said polarization analyzer is configured to rotate.

15. The system as in claim 12, wherein said first and second gratings are spaced relative to each other in an optical path of said first reflected probe beam and configured to produce a predetermined phase manipulation on a wavefront of said first reflected probe beam, wherein said first detector module further includes:
a lens positioned to receive said first reflected probe beam from said first and second gratings and configured to select and combine two diffraction components from said second grating to produce an interference pattern, wherein said selected two diffraction components are produced by said second grating from diffracting two different diffraction components from said first grating and are substantially parallel to each other, and
wherein said a first optical sensing array is disposed relative to said lens to receive said interference pattern and produce an electrical signal indicative of said interference pattern.

16. A method, comprising:

illuminating a sample having a specularly reflective sample surface with a collimated coherent probe beam to produce a reflected probe beam that has information about said sample;

splitting said reflected probe beam into a first portion and a second portion that have said same information;

processing said first portion to obtain a curvature of said sample surface from said same information; and processing said second portion to obtain another property of said sample from said same information.

17. The method as in claim 16, wherein a change in polarization of said reflected probe beam is measured in processing said second portion.

18. The method as in claim 17, wherein said another property of said sample includes a thickness of a film formed said sample surface.

19. The method as in claim 17, wherein said another property of said sample includes a refractive index.

20. The method as in claim 17, wherein said another property of said sample includes an optical absorption coefficient.

21. The method as in claim 17, wherein said another property of said sample includes a stress.

22. The method as in claim 16, wherein the processing of said second portion includes:

diffracting said second portion by first and second gratings spaced relative to each other in an optical path of said first reflected probe beam to produce a predetermined phase manipulation on a wavefront of said first portion, combining two diffraction components from said second grating to produce an interference pattern, wherein said selected two diffraction components are produced by said second grating from diffracting two different diffraction components from said first grating and are substantially parallel to each other, processing said interference pattern to extract a spatial gradient information on the wavefront of said reflected probe beam caused by a curvature of the reflective surface, and determining said curvature of the reflective surface according to said spatial gradient information.

23. The method as in claim 16, wherein said sample surface is a flat mirror, and further comprising using an error in a measurement of said property to determine a degree of collimation of said probe beam.

24. A method, comprising:

illuminating a sample having a specularly reflective sample surface with a collimated coherent probe beam to produce a reflected probe beam that has information about said sample;

controlling polarization of said probe beam at a desired input polarization prior to incidence upon said sample surface;

performing an ellipsometric measurement on a first portion of said reflected probe beam;

measuring a second portion of said reflected probe beam to obtain a curvature of said sample surface from said information; and processing said ellisometric measurement by using said curvature to determine a property of said sample.

25. The method as in claim 24, wherein said property includes a thickness of a film formed on said sample.

26. The method as in claim 24, wherein said property includes a stress on said sample.

27. The method as in claim 24, further comprising using said ellipsometric measurement to determine a degree of collimation of said probe beam.

28. The method as in claim 24, wherein said curvature is measured by diffracting said second portion of said reflected probe beam through two optical gratings and measuring an interference signal produced by combining two selected diffracted signals.

29. The method as in claim 24, further comprising measuring an optical property of said first portion of said reflected probe beam to infer whether a location on said sample surface is concave or convex.

* * * * *